United States Patent [19]

Staton et al.

[11] Patent Number: 5,104,843
[45] Date of Patent: Apr. 14, 1992

[54] CATALYST COMPOSITION FOR COUPLING PROCESS

[75] Inventors: James S. Staton; Michael D. Standiford, both of Orangeburg, S.C.; David A. Rockstraw, Ponca City, Okla.

[73] Assignee: Ethyl Corporation, Richmond, Va.

[21] Appl. No.: 611,834

[22] Filed: Nov. 13, 1990

[51] Int. Cl.$^5$ .......................................... B01J 27/232
[52] U.S. Cl. .................................................. 502/174
[58] Field of Search ........................................ 502/174

[56] References Cited

U.S. PATENT DOCUMENTS

| | | | |
|---|---|---|---|
| 3,624,177 | 11/1971 | Lowther | 502/174 X |
| 4,916,100 | 4/1990 | Knuuttila et al. | 502/174 |
| 4,977,124 | 12/1990 | Smith | 502/174 |

FOREIGN PATENT DOCUMENTS 1269280  4/1972  United Kingdom .

Primary Examiner—W. J. Shine
Attorney, Agent, or Firm—Richard J. Hammond

[57] ABSTRACT

A catalyst composition having enhanced effectiveness in coupling an alkene with an aromatic hydrocarbon having an active hydrogen on a saturated α-carbon is obtained by treating an alkali metal with an alkali metal carbonate.

2 Claims, No Drawings

CATALYST COMPOSITION FOR COUPLING PROCESS

FIELD OF INVENTION

This invention relates to catalyst compositions and, more particularly, to catalyst compositions which can be used in the coupling of alkenes with aromatic hydrocarbons having an active hydrogen on a saturated $\alpha$-carbon.

BACKGROUND

U.S. Pat. No. 4,179,580 (Cobb), European Patent 128001 (Kudoh, et al.), and Eberhardt, et al., *Journal of Organic Chemistry*, Vol. 30, pp. 82-84 (1965) show that it is known that supported alkali metals are useful as catalysts in the coupling of ethylenically-unsaturated hydrocarbons with aromatic hydrocarbons having an active hydrogen on a saturated $\alpha$-carbon. The supported alkali metals are more effective than the corresponding unsupported alkali metals in such reactions but are still not as effective as might be desired.

As disclosed in co-pending applications Ser. No. 135,318 (Smith, filed Dec. 21, 1987, now abandoned and Ser. No. 276,531 (Smith), Ser. No. 276,532 (Smith), and Ser. No. 276,533 (Smith), filed Nov. 28, 1988, all now abandoned, it has been found that alkenes can advantageously be coupled with $\alpha$-carbon in the presence of a supported alkali metal as a catalyst and about 10-100 mole %, based on the amount of the alkali metal catalyst, of an oxide of sodium, potassium, rubidium, cesium, barium, strontium, calcium, or magnesium as a co-catalyst.

U.K. Pat. 1,269,280 discloses a process for the manufacture of alkyl aromatic hydrocarbons using a catalyst prepared by dispersing sodium and/or lithium or an anhydrous potassium compound The dispersing is carried out by stirring or tumbling the molten metal with the potassium compound, the potassium compound being selected so that it does not melt, sinter or decompose at the deposition temperature.

SUMMARY OF INVENTION

An object of this invention is to provide a novel catalyst composition.

Another object of this invention is to provide a novel catalyst composition which is effective in catalyzing the coupling of an alkene with an aromatic hydrocarbon having an active hydrogen on a saturated $\alpha$-carbon.

These and other objects are attained by treating an alkali metal with an alkali metal carbonate.

DETAILED DESCRIPTION

The alkali metal employed in the practice of the invention may be lithium, sodium, potassium, rubidium, or cesium. It is preferably sodium.

The alkali metal carbonates used with the above-disclosed alkali metal are the carbonates of lithium, sodium, potassium, rubidium, or cesium. While any of the above alkali metal carbonates can be used with any of the above alkali metals, it is preferred that the alkali metal be different than the alkali metal moiety of the alkali metal carbonate. Particularly preferred are catalysts comprising sodium and potassium carbonate or potassium and sodium carbonate.

In mixing the alkali metal and the alkali metal carbonate, it is useful to have the alkali metal in the liquid (melted) form, which permits a catalyst to readily form. It is essentially a liquid heterogeneous mixture when at high temperature (the liquid metal is absorbed onto the surface of the solid) but a solid heterogeneous mixture at lower temperatures. The melting point of such mixture depends, of course, on the type of alkali metal and alkali metal carbonate, as well as the mole ratio of such components, e.g., mixtures of sodium and potassium carbonate, (at a mole ratio of 1:1) melt at about 100° C. Thus, for example, a catalyst from rubidium metal and potassium carbonate is prepared by heating rubidium to about 40° C. and adding potassium carbonate. The mixture is a solid at room temperature.

Among the important conditions for forming the catalysts of the present invention (aside from temperature of processing) are included the ratios of the alkali metal to the alkali metal carbonate and the size of the alkali metal carbonate granules. Thus, mole ratios of alkali metal to alkali metal carbonate used to prepare the catalyst compositions are from about 0.5 to 1 to about 4 to 1. Preferably, this ratio is from about 1 to 1, to 3 to 1, most preferably from about 2 to 1 to about 3 to 1.

The size of the granules of alkali metal carbonate must not be so coarse as to inhibit the formation of a satisfactory catalyst. Such granules merely need to be small enough to provide sufficient surface area for the liquid metal to coat the solid so that metal and carbonate can react. Thus, the size can be as large as 5 mm with smaller granules, 0.05 mm, being preferred. The rate of mixing the particles is not critical in achieving an improved catalyst composition. However, the agitation rate must be sufficient to provide thorough mixing of the two phases as well as good heat transfer.

While not wishing to be bound by the following, it is believed that the melted alkali metal reacts with the alkali metal carbonate to form a complex mixture of alkali metal alloy and carbonate. The complex mixture is a more effective catalyst than the alkali metal alone or the prior art alkali metal alloys (NaK alloy).

When the novel catalyst composition is employed in a coupling reaction, it is used in an amount such as to provide a catalytic amount of the alkali metal, generally about 2-10 mole %, based on the amount of either of the reactants when they are utilized in equimolar amounts or on the amount of the major reactant when they are not utilized in equimolar amounts.

As in the processes of Smith, the alkene which is coupled with the aromatic hydrocarbon in the presence of the catalyst composition may be any of the alkenes which are known to be useful in such reactions, such as ethene, propene, 1-butene, 2-butene, isobutene, 1-pentene, 2-pentene, 3-methyl-1-butene, 2-methyl-2-butene, 1-hexene, 2-hexene, 3-hexene, 4-methyl-1-pentene, 3-methyl-1-pentene, 4-methly-2-pentene, 2-heptene, 2-octene, 4-nonene, 1-decene, 2-decene, 1-dodecene, 3-tetradecene, 5-hexadecene, 6-methyl-4-heptadecene, 1-eicosene, etc. However, it is generally an alkene corresponding to the formula QQ'C=CTT', in which Q, Q', T, and T' are independently selected from hydrogen and alkyl groups of up to 20 carbons; and it is apt preferably to be an alkene of up to 20 carbons. Particularly preferred alkenes are ethene and propene.

The aromatic hydrocarbon having an active hydrogen on a saturated $\alpha$-carbon may be any such compound that is known to be useful in such reactions, such as toluene, ethylbenzene, n-propylbenzene, isopropylbenzene, n-butylbenzene, secbutylbenzene, isobutylbenzene, n-eicosylbenzene, o-, m-, and p-xylenes, o-, m-, and p-ethyltoluenes, 1,3,5-trimethylbenzene, 1,2,3,4- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula RR'R"CH, in which R is an aryl group of up to 20 carbons and R' and R" are independently selected from hydrogen and alkyl and aryl groups of up to 20 carbons; and it is apt preferably to be an alkylbenzene having one or more ar-alkyl groups. A particularly preferred aromatic hydrocarbon is toluene.

The mole ratio of alkene to aromatic hydrocarbon in these coupling reactions varies with the particular reactants employed and the products desired, particularly since the aromatic hydrocarbon may have one or more active hydrogens, and it may be desired to react the alkene with only one or with more than one active hydrogen in the aromatic hydrocarbon. It is frequently preferred to employ the reactants in the stoichiometric amounts appropriate for the preparation of the desired product. However, either reactant can be used in excess.

The coupling reaction is conducted by heating a mixture of the alkene, the active hydrogen-containing aromatic hydrocarbon, and the novel catalyst composition under substantially anhydrous conditions at a suitable temperature, generally about 100°–300° C., preferably about 175°–200° C., to couple the reactants. It is generally conducted in the absence of a diluent or in the presence of an excess of the active hydrogen-containing aromatic hydrocarbon as the sole diluent. However, an inert diluent can be used if desired. Exemplary of such diluents are liquid alkanes, cycloalkanes, and aromatic hydrocarbons, such as pentane, hexane, isooctaine, cyclohexane, naphthalene, decahydronaphthalene, white oils, etc.

The catalyst compositions of the invention are advantageous in that they provide a more economically reliable composition, producing higher product yields when used in coupling reactions than comparable more expensive catalyst compositions, e.g., sodium-potassium alloy. The coupling reactions in which these catalysts are used are particularly advantageous as a means of alkylating alkylaromatic compounds, especially alkylbenzenes, to form compounds useful as solvents, internal standards, intermediates for polymers, pharmaceuticals, or pesticides, etc.

The following examples are given to illustrate the invention and are not intended as a limitation thereof.

COMPARATIVE EXAMPLE 1

A suitable reaction vessel was sequentially charged with 10 g of alumina having a surface area of 4 m²/g, 92 g of toluene, and 1.0 g of NaK (an alloy having a K content of 78% by weight). The mixture was stirred and heated to 185° C., after which propene was charged until a pressure of 400 psig was reached. During the reaction the stirrer was stopped periodically to allow the solids to settle; and samples were drawn, allowed to cool to room temperature, and subjected to GC analysis to determine the amounts of unreacted toluene, desired isobutylbenzene (IBB) product, and n-butylbenzene (NBB) and methylindan (MI) by-products. The results of the analyses are shown below.

| Time (min.) | Moles × 100 | | | |
| --- | --- | --- | --- | --- |
| | Toluene | IBB | NBB | MI |
| 40 | 81.1 | 11.1 | 0.43 | 3.66 |
| 120 | 62.1 | 21.9 | 0.89 | 6.55 |
| 200 | 54.5 | 25.1 | 1.01 | 7.13 |
| 240 | 53.2 | 25.5 | 1.04 | 7.18 |

COMPARATIVE EXAMPLE 2

Comparative Example 1 was repeated except that 0.26 g of −325 mesh powdered sodium oxide was charged to the reaction vessel after the charging of the alumina. The results of th analyses are shown below.

| Time (min.) | Moles × 100 | | | |
| --- | --- | --- | --- | --- |
| | Toluene | IBB | NBB | MI |
| 40 | 99.8 | 0.4 | 0.04 | 0 |
| 120 | 82.8 | 8.4 | 1.09 | 0.14 |
| 200 | 48.5 | 34.8 | 4.19 | 0.50 |
| 240 | 33.1 | 45.8 | 5.33 | 0.54 |

COMPARATIVE EXAMPLE 3

81 grams of commercial grade sodium/potassium alloy having a composition of 78 weight % potassium and 22 weight % sodium was charged to a 5 gal autoclave purged with nitrogen. 2 grams of Emersol 213 grade oleic acid and 8107 grams of commercial grade toluene were added. The mixture was heated to 190° C. with high shear agitation at a tip speed of 29 ft/sec. When the mixture reached 190° C., addition of propylene was started, maintaining the reactor pressure between 350 and 400 psig. When 2985 grams of propylene had been added, propylene addition was stopped. The reactor was held at 190° C. to give a total reaction time of 3 hours (which included the propylene feed time). The reactor was then cooled to 30° C. and the contents washed with water to de-activate any remaining catalyst. Analysis of the organic phase by gas chromatography gave the following results:

| | Weight % |
| --- | --- |
| light ends | 3.3 |
| toluene | 31.9 |
| isobutylbenzene | 54.6 |
| normalbutylbenzene | 5.5 |
| heavy ends | 4.6 |

COMPARATIVE EXAMPLE 4

80 grams of commercial grade sodium was charged to a 1 liter autoclave purged with nitrogen. 428 grams of commercial grade toluene were added. The mixture was heated to 190° C. with high shear agitation at a tip speed of 22 ft/sec. When the mixture reached 190° C., addition of propylene was started to give a reactor pressure of 400 psig. Only 60 grams of propylene could be added over a four hour period since the reactor pressure remained at 400 psig. The reactor was then cooled to 30° C. and the contents washed with water to deactivate any remaining catalyst. Analysis of the organic phase by gas chromatography gave the following results:

| Weight % | |
|---|---|
| light ends | 1.4 |
| toluene | 98.6 |
| isobutylbenzene | 0.0 |
| normalbutylbenzene | 0.0 |
| heavy ends | 0.0 |

EXAMPLE 1

60 grams of sodium metal was charged to a 1-liter glass round bottom flask equipped with an agitator, heating mantle, temperature indicator and nitrogen purge. The reactor was heated until all the sodium had melted (around 110° C.) and agitation was started. As the sodium was heating at 300° C., 320 grams of 99+% anhydrous granular potassium carbonate was added and the mixture was agitated at 300° C. for 1 hour. The reaction mass was then allowed to cool to room temperature under a nitrogen purge and was transferred from the reactor to a glass container in a nitrogen filled glove box.

265 grams of the above catalyst was charged to a 5 gal. autoclave purged with nitrogen. 2 grams of Emersol 213 grade oleic acid and 8107 grams of commercial grade toluene were added. The mixture was heated to 190° C. with high shear agitation at a tip speed of 29 ft/sec. When the mixture reached 190° C., addition of propylene was started, maintaining the reactor pressure between 350 and 400 psig. When 2985 grams of propylene had been added, propylene addition was stopped. The reactor was held at 190° C. to give a total reaction time of 8 hours (which included the propylene feed time). The reactor was then cooled to 30° C. and the contents washed with water to deactivate an remaining catalyst. Analysis of the organic phase by gas chromatography gave the following results:

| Weight % | |
|---|---|
| light ends | 2.0 |
| toluene | 36.4 |
| isobutylbenzene | 53.1 |
| normalbutylbenzene | 4.9 |
| heavy ends | 3.6 |

EXAMPLE 2

60 grams of sodium metal was charged to a 1-liter glass round bottom flask equipped with an agitator, heating mantle, temperature indicator and nitrogen purge. The reactor was heated until all the sodium had melted (around 110° C.) and agitation was started. As the sodium was heating to 300° C., 270 grams of 99+% anhydrous powdered potassium carbonate was added and the mixture was agitated at 310° C. for 1 hour. The reaction mass was then allowed to cool to room temperature under a nitrogen purge and was transferred from the reactor to a glass container in a nitrogen filled glove box.

265 grams of the above catalyst was charged to a 5 gal. autoclave purged with nitrogen. 2 grams of Emersol 213 grade oleic acid and 8107 grams of commercial grade toluene were added. The mixture was heated to 190° C. with high shear agitation at a tip speed of 30 ft/sec. When the mixture reached 190° C., addition of propylene was started, maintaining the reactor pressure between 350 and 400 psig. When 2985 grams of propylene had been added, propylene addition was stopped. The reactor was held at 190° C. to give a total reaction time of 6 hours (which included the propylene feed time). The reactor was then cooled to 30° C. and the contents washed with water to deactivate any remaining catalyst. Analysis of the organic phase by gas chromatography gave the following results:

| Weight % | |
|---|---|
| light ends | 3.3 |
| toluene | 34.9 |
| isobutylbenzene | 52.5 |
| normalbutylbenzene | 3.8 |
| heavy ends | 5.5 |

EXAMPLE 3

60 grams of sodium metal was charged to a 1-liter glass round bottom flask equipped with an agitator, heating mantle, temperature indicator and nitrogen purge. The reactor was heated until all the sodium had melted (around 110° C.) and agitation was started. As the sodium was heating to 300° C., 320 grams of 99+% anhydrous granular potassium carbonate was added and the mixture was agitated at 300° C. for 1 hour. The reaction mass was then allowed to cool to room temperature under a nitrogen purge and was transferred from the reactor to a glass container in a nitrogen filled glove box.

266 grams of the above catalyst was charged to a 5 gal. autoclave purged with nitrogen. 2 grams of Emersol 213 grade oleic acid and 8107 grams of toluene that was distilled from the reaction product of earlier runs were added. The mixture was heated to 190° C. with high shear agitation at a tip speed of 29 ft/sec. When the mixture reached 190° C., addition of propylene was started, maintaining the reactor pressure between 350 and 400 psig. When 2985 grams of propylene had been added, propylene addition was stopped. The reactor was held at 190° C. to give a total reaction time of 8 hours (which included the propylene feed time). The reactor was then cooled to 30° C. and the contents washed with water to deactivate any remaining catalyst. Analysis of the organic phase by gas chromatography gave the following results:

| Weight % | |
|---|---|
| light ends | 1.4 |
| toluene | 38.1 |
| isobutylbenzene | 52.5 |
| normalbutylbenzene | 3.4 |
| heavy ends | 2.8 |

EXAMPLE 4

74 grams of sodium metal was charged to a 1-liter glass round bottom flask equipped with an agitator, heating mantle, temperature indicator and nitrogen purge. The reactor was heated until all the sodium had melted (around 110° C.) and agitation was started. As the sodium was heating to 350° C., 160 grams of 99+% anhydrous powdered potassium carbonate was added and the mixture was agitated at 350° C. for 1 hour. The reaction mass was then allowed to cool to room temperature under a nitrogen purge and was transferred from the reactor to a glass container in a nitrogen filled glove box.

227 grams of the above catalyst was charged to a 5 gal. autoclave purged with nitrogen. 2 grams of Emersol 213 grade oleic acid and 8107 grams of commercial grade toluene were added. The mixture was heated to 190° C. with high shear agitation at a tip speed of 30 ft/sec. When the mixture reached 190° C., addition of propylene was started, maintaining the reactor pressure between 350 and 400 psig. When 2985 ggrams of propylene had been added, propylene addition was stopped. The reactor was held at 190° C. to give a total reaction time of 4 hours (which included the propylene feed time). The reactor was then cooled to 30° C. and the contents washed with water to deactivate any remaining catalyst. Analysis of the organic phase by gas chromatography gave the following results:

| | Weight % |
|---|---|
| light ends | 2.8 |
| toluene | 36.0 |
| isobutylbenzene | 52.9 |
| normalbutylbenzene | 3.6 |
| heavy ends | 4.8 |

EXAMPLE 5

38 grams of sodium metal was charged to a 1-liter glass round bottom flask equipped with an agitator, heating mantle, temperature indicator and nitrogen purge. The reactor was heated until all the sodium had melted (around 110° C.) and agitation was started. As the sodium was heating to 300° C., 227 grams of 99+% anhydrous granular potassium carbonate was added and the mixture was agitated at 300° C. for 1 hour. The reaction mass was then allowed to cool to room temperature under a nitrogen purge and was transferred from the reactor to a glass container in a nitrogen filled glove box.

15 grams of catalyst from the above batch were charged to a 1-liter autoclave purged with nitrogen. 428 grams of commercial grade toluene were added. The mixture was heated to 190° C. with high shear agitation at a tip speed of 22 ft/sec. When the mixture reached 190° C., addition of propylene was started, maintaining the reactor pressure between 350 and 400 psig. When 133 grams of propylene had been added, propylene addition was stopped. The reactor was held at 190° C. to give a total reaction time of 5 hours (which included the propylene feed time). The reactor was then cooled to 30° C. and the contents washed with water to deactivate any remaining catalyst. Analysis of the organic phase by gas chromatography gave the following results:

| | Weight % |
|---|---|
| light ends | 0.4 |
| toluene | 54.7 |
| isobutylbenzene | 38.6 |
| normalbutylbenzene | 3.7 |
| heavy ends | 2.6 |

We claim:
1. A catalyst composition suitable for coupling an alkene with an aromatic hydrocarbon having an active hydrogen atom on a saturated α-carbon atom prepared by heating a melt of an alkali metal selected from the group consisting essentially of lithium, sodium, potassium, rubidium and cesium with an alkali metal carbonate selected from the group consisting essentially of the carbonates of lithium, sodium, potassium, rubidium and cesium, wherein the ratio of said alkali metal to alkali metal carbonate is from about 0.5 to 1 to about 4 to 1.
2. The composition according to claim 1 wherein said alkali metal is sodium and said alkali metal carbonate is potassium carbonate.

* * * * *